United States Patent
Bajaj et al.

(10) Patent No.: US 9,433,919 B2
(45) Date of Patent: Sep. 6, 2016

(54) ACTIVATED CARBON-METAL ORGANIC FRAMEWORK COMPOSITE MATERIALS WITH ENHANCED GAS ADSORPTION CAPACITY AND PROCESS FOR THE PREPARATION THEREOF

(75) Inventors: Hari Chand Bajaj, Bhavnagar (IN); Rajesh Shantilal Somani, Bhavnagar (IN); Phani Brahma Rallapalli, Bhavnagar (IN); Dinesh Patil, Bhavnagar (IN); Karikkethu Prabhakaran Prasanth, Bhavnagar (IN); Checkalazhikathu Raj Manoj, Bhavnagar (IN); Rajendra Singh Thakur, Bhavnagar (IN); Mathew John, Greater Noida (IN); Bharat Lakshman Newalkar, Greater Noida (IN); Nettem Venkateswarlu Choudary, Greater Noida (IN)

(73) Assignees: Council of Scientific & Industrial Research, New Delhi (IN); Bharat Petroleum Corporation Limited, Mumbai (IN)

( * ) Notice: Subject to any disclaimer, the term of this patent is extended or adjusted under 35 U.S.C. 154(b) by 67 days.

(21) Appl. No.: 14/006,729

(22) PCT Filed: Mar. 30, 2012

(86) PCT No.: PCT/IB2012/000641
§ 371 (c)(1),
(2), (4) Date: Sep. 23, 2013

(87) PCT Pub. No.: WO2012/131483
PCT Pub. Date: Oct. 4, 2012

(65) Prior Publication Data
US 2014/0018238 A1    Jan. 16, 2014

(30) Foreign Application Priority Data
Mar. 31, 2011    (IN) ............ 0919/DEL/2011

(51) Int. Cl.
*C01B 31/08* (2006.01)
*B01J 20/22* (2006.01)
*B01J 20/20* (2006.01)
*B01J 20/30* (2006.01)
*C07C 51/41* (2006.01)
*F17C 11/00* (2006.01)

(52) U.S. Cl.
CPC ............ *B01J 20/223* (2013.01); *B01J 20/20* (2013.01); *B01J 20/226* (2013.01); *B01J 20/3064* (2013.01); *C07C 51/418* (2013.01); *F17C 11/00* (2013.01); *F17C 11/005* (2013.01); *B01J 2220/40* (2013.01); *Y02C 10/08* (2013.01); *Y02E 60/321* (2013.01)

(58) Field of Classification Search
CPC ............... B01J 20/20; B01J 20/226
See application file for complete search history.

(56) References Cited

U.S. PATENT DOCUMENTS 5,639,707 A    6/1997 Lewis et al.
8,647,419 B2 *  2/2014 Kaskel ............... 96/134

FOREIGN PATENT DOCUMENTS

EP    2341031 A1    7/2011

OTHER PUBLICATIONS

N. Stock et al. "Synthesis of Metal-Organic Frameworks (MOFs): Routes to Various MOF Topologies, Morphologies and Composites," Chem Rev. 112, 933-969 (2012).
C. Petit et al. "The Synthesis and characterization of copper-based metal-organic framework/graphite oxide composites,"Carbon 49, 563-572 (2011).
P. B. S. Rallapalli et al. "Activated carbon @ MIL-101(Cr(: a potential metal-organic framework composite material for hydrogen storage," Int. J. Energy Res. (2011).
I. Senkovska et al. "High pressure methane adsorption in the metal-organic frameworks $Cu_3(btc)_2$, $Zn_2(bdc)_2dabco$, and $Cr_3F(H_2O)_2O(bdc)_3$,"Microporous and Mesoporous Materials 112, 108-115, (2008).
Z. Xiang et al. "Metal-Organic Frameworks with Incorporated Carbon Nanotubes: Improving Carbon Dioxide and Methane Storage Capacities by Lithium Doping," Angew. Chem. Int. Ed. 50, 491-494, (2011).
International Search Report and Written Opinion issued in PCT/IB2012/000641, dated Aug. 1, 2012.

* cited by examiner

*Primary Examiner* — Stuart Hendrickson
(74) *Attorney, Agent, or Firm* — Locke Lord LLP; Barry Kramer; Nicholas J. DiCeglie, Jr.

(57) ABSTRACT

The present invention discloses activated carbon-metal organic framework composite materials (AC@MOF) with enhanced gas adsorption capacity. The present invention also discloses a process for the preparation of carbon-metal organic framework composite materials (AC@MOF). The present invention involves the use of "void space filling method" in metal organic frameworks (MOFs), which have been accomplished by in-situ addition of selected type and appropriate amount of activated carbon during the synthesis of MOF such as Cu-BTC, in the storage of gases such as methane. The gas adsorption capacity of these AC@MOF composite materials is significantly increased through this method.

6 Claims, 4 Drawing Sheets

ACTIVATED CARBON-METAL ORGANIC FRAMEWORK COMPOSITE MATERIALS WITH ENHANCED GAS ADSORPTION CAPACITY AND PROCESS FOR THE PREPARATION THEREOF

CROSS REFERENCE TO RELATED APPLICATIONS

This application is a 371 U.S. National Phase Application of PCT/IB2012/000641, filed Mar. 30, 2012, which claims priority to Indian Patent Application No. 0919/DEL/2011, filed Mar. 31, 2011, the disclosures of each of which are expressly incorporated herein by reference in their entireties.

FIELD OF INVENTION

The present invention relates to provide activated carbon-metal organic framework composite materials (AC@MOF) with enhanced gas adsorption capacity. More specifically, it relates to a process for the preparation of metal organic frameworks (MOF) in the presence of selected type and appropriate amount of activated carbon to provide increased gas adsorption capacity for methane as compared to MOF that have been synthesized without activated carbon.

BACKGROUND OF THE INVENTION

Natural gas (NG) having methane as major component has already been known as potential fuel for vehicular application. Vehicles running on compressed natural gas (CNG) are on the roads. However, there are pros and cons associated with use of CNG. The alternate lies in the use of adsorbed natural gas (ANG). Considering the potential of ANG, the Department of Energy (DoE) in the United States has set targets as 180 v(STP)/v, at 3.5 MPa and 298 K [STP is standard temperature (298 K) and pressure (0.1 MPa)], for methane storage in vehicular application. Research on developing efficient materials and enhancing the capacity of known materials such as porous silicates, carbons, and MOFs have been pursued as means for methane storage. Although each of the prior art work to some extent, more efficient storage materials are necessary to cope with the DoE targets. The highest methane storage capacity obtained in activated carbons is ca. 200 v/v [Wegrzyn, J., and Gurevich, M., "Adsorbent storage of natural gas", Appl. Energy, 55, 71-83 (1996)], although significant efforts were made on processing activated carbons.

Metal organic-frameworks (MOFs) are a new class of nanoporous materials that have potential applications in separation processes, catalysis and gas storage. MOFs are synthesized using organic linker molecules and metal clusters that self-assemble to form materials with well defined pores, high surface areas, and desired chemical functionalities. Because of these attractive properties, MOFs are promising candidates for $CO_2$ capture, as well as methane and hydrogen storage.

A variety of MOFs have been screened for methane storage [Wang, S., "Comparative molecular simulation study of methane adsorption in metal-organic frameworks", Energy & Fuels, 21, 953-956 (2007); Noro, S., Kitagawa, S., Kondo, M., Seki, K., "A new, methane adsorbent, porous coordination polymer [{$CuSiF_6$(4,4'-bipyridine)2}n]", Angew. Chem. Int. Ed., 39, 2081-2084 (2000); Kondo, M., Shimamura, M., Noro, S. I., Minakoshi, S., Asami, A., Seki, K., Kitagawa, S., "Microporous materials constructed from the interpenetrated coordination networks. Structures and methane adsorption properties", Chem. Mater., 12, 1288-1299 (2000); Bourrelly, S., Llewellyn, P. L., Serre, C., Millange, F., Loiseau, T., Ferey, G., "Different adsorption behaviors of methane and carbon dioxide in the isotopic nanoporous metal terephthalate MIL-53 and MIL-47", J. Am. Chem. Soc., 127, 13519-13521 (2005); Düren, T., Sarkisov, L., Yaghi, O. M., Snurr, R. Q., "Design of new materials for methane storage", Langmuir, 20, 2683-2689 (2004); Ma, S., Sun, D., Simmons, J. M., Collier, C. D., Yuan, D., Zhou, H. C., "Metal-organic framework from an anthracene derivative containing nanoscopic cages exhibiting high methane uptake", J. Am. Chem. Soc., 130, 1012-1016 (2008).], but only a few can reach the DoE target. For example, Düren et al. ["Düren, T., Sarkisov, L., Yaghi, O. M., Snurr, R. Q. Design of new materials for methane storage", Langmuir, 20, 2683-2689 (2004)] proposed a theoretical MOF (IRMOF-993) with a methane adsorption capacity of 181 v(STP)/v. Ma et al. [Ma, S., Sun, D., Simmons, J. M., Collier, C. D., Yuan, D., Zhou, H. C., "Metal-organic framework from an anthracene derivative containing nano-scopic cages exhibiting high methane uptake", J. Am. Chem. Soc., 130, 1012-1016 (2008)] synthesized a MOF named PCN-14 that gave the highest methane adsorption capacity of 230 v(STP)/v so far. However, they used crystal density rather than packed density in arriving at this value.

Catenated MOFs are composed of two mutually catenated frameworks that generate additional pores with various sizes. The catenation structure strengthens the gas affinity for the material by an entrapment mechanism that improves the gas adsorption capacity and separation. Thus, catenation appeared to be a useful strategy for designing new MOFs as efficient methane storage materials. Based on this consideration, a systematic molecular simulation study is performed to investigate the effect of catenation on methane storage capacity to provide useful information for further MOFs development with improved methane storage capacity. [XUE Chunyu, ZHOU Zi'e, YANG Qingyuan and ZHONG Chongli, Enhanced Methane Adsorption in Catenated Metal-organic Frameworks: A Molecular Simulation Study, Chinese Journal of Chemical Engineering, 17(4) 580-584 (2009)]. This work also showed that catenated MOFs can meet the DoE target easily for methane storage, indicating that the creation of catenated frameworks is a promising strategy for developing MOF-based efficient methane storage materials in vehicular applications. However, it is still theoretical study and no report published till date to prove such strategy.

U.S. Pat. No. 7,196,210 (Omar M. Yaghi, et al., Mar. 27, 2007) describes isoreticular metal-organic frameworks, process for forming the same and systematic design of pore size and functionality therein, with application for gas storage. An inventive strategy based on reticulating metal ions and organic carboxylate links into extended networks has been advanced to a point that has allowed the design of porous structures in which pore size and functionality can be varied systematically. MOF-5, a prototype of a new class of porous materials and one that is constructed from octahedral Zn—O—C clusters and benzene links, was used to demonstrate that its 3-D porous system can be functionalized with the organic groups. Indeed, the data indicate that members of this series represent the first mono crystalline mesoporous organic/inorganic frameworks, and exhibit the highest capacity for methane storage (155 $cm^3/cm^3$ at 36 atm.) and the lowest densities (0.41 to 0.21 $g/cm^3$) attained to date for any crystalline material at room temperature. The drawback associated with this material is its low densities which result in less amount of material in a fixed volume.

US 20100069234, (Richard R. Willis, John J. Low, Syed A. Faheem, Annabelle I. Benin, Randall Q. Snurr, and Ahmet Ozgur Yazaydin, describes the use of certain metal organic frameworks that have been treated with water or another metal titrant in the storage of carbon dioxide. The capacity of these frameworks is significantly increased through this treatment. The limitation of this invention is that the method is shown suitable for storage of carbon dioxide and it does not teach about methane storage.

In the present invention, it is shown that MOFs, specifically Cu-BTC, can be easily tuned to significantly enhance methane storage capacity simply by synthesizing the Cu-BTC in presence of selected type and appropriate amount of activated carbon there by filling the void space. This method for enhanced storage of methane may apply to certain other guest molecules and other MOFs also.

It is common practice to activate MOFs at about above 150° C. to remove the solvent and open up the void space for the adsorption of desired gas molecules. If the evacuation temperature is high enough, all guest molecules entrapped during the synthesis can be removed, including those that are coordinatively bound to framework metal atoms. Removing these coordinated solvent molecules leaves coordinatively-unsaturated, open-metal sites that have been shown to promote gas uptake, especially for $H_2$ adsorption. Recently, Bae et al. [Youn-Sang Bae, Omar K. Farha, Alexander M. Spokoyny, Chad A. Mirkin, Joseph T. Hupp and Randall Q. Snurr, Chem. Commun., 2008, 4135-4131] showed that in a carborane-based MOF removal of coordinated dimethyl formamide increased $CO_2$ and $CH_4$ adsorption and led to high selectivity for $CO_2$ over methane. The open-metal sites in MOFs are reminiscent of the extra-framework cations in zeolites, in that they are expected to create large electric fields and to readily bind polar molecules. Methane being non-polar molecule is adsorbed in the overlapping force field created between two walls of a pore.

Cu-BTC (also known as HKUST-1) is a well-studied MOF, first synthesized by Chui et al. [S. S.-Y. Chui, S. M.-F. Lo, J. P. H. Charmant, A. G. Orpen, I. D. Williams, Science 283 (1999) 1148-1150]. The structure of Cu-BTC is composed of large central cavities (diameter 9.0 Å) surrounded by small pockets (diameter 5.0 Å), connected through triangular-shaped apertures of similar size. The Cu-BTC framework has paddlewheel type metal corners connected by benzene-1,3,5-tricarboxylate (BTC) linkers. Each metal corner has two copper atoms bonded to the oxygen of four BTC linkers. In the as-synthesized material, each copper atom is also coordinated to one water molecule. MOFs have been found to have the capacity to store methane readily and at high selectivity over other gases such as nitrogen. In research publications, several MOFs that have the capacity to store methane are described. However, the storage capacity is not matching to the DoE targets, and therefore, it is necessary to enhance the capacity for methane storage to make them commercially useful.

In the present invention, a process has been developed and described for enhancing the gas storage capacity of MOFs, and especially for methane on Cu-BTC, by using "void space filling method" that have been accomplished simply by in-situ addition of selected type and appropriate amount of activated carbon, as 'void space filling agent', during the synthesis of Cu-BTC, thereby forming composite materials, AC@MOF. The gas storage capacity of this AC@MOF composite material is significantly increased as compared to the MOF synthesized without activated carbon.

OBJECTIVE OF PRESENT INVENTION

The main objective of present invention is to provide activated carbon-metal organic framework composite materials (AC@MOF) with enhanced gas adsorption capacity. Another objective of the present invention is to provide a process for the preparation of activated carbon-metal organic framework composite materials (AC@MOF) with enhanced gas adsorption capacity.

SUMMARY OF THE INVENTION

Accordingly, the present invention provides activated carbon-metal organic framework composite materials having general formula $[Cu_3(BTC)_2.(H_2O)_x.(AC)_y]_n$, AC=activated carbon, with the elemental composition in the range C, 32 to 34 wt %; H, 1.90 to 2.20%; and M, 26 to 28% by wt.

In one embodiment of the present invention activated carbon-metal organic framework composite materials are useful for storage of gases.

In another embodiment of the present invention said gas is selected from the Natural gas, methane, carbon dioxide and hydrogen.

In another embodiment of the present invention enhancement of methane adsorption capacity of activated carbon-metal organic framework composite materials ranges between 20 wt % to 95 wt % as compared to metal organic framework prepared without using activated carbon.

In another embodiment of the present invention a process for the preparation of activated carbon-metal organic framework composite materials with enhanced gas adsorption capacity, wherein the said process comprising the steps:
a) dissolving an organic ligand in an alcohol, preferably ethanol;
b) dissolving a metal salt in the water;
c) mixing solution as obtained in step (a) with solution as obtained in step (b) followed by stirring at temperature ranging from 298K to 308K for a period ranging between 10 to 50 min;
d) transferring the reaction mixture as obtained in step (c) into an autoclave and further adding activated carbon in the range 1 to 3% in respect of weight of product followed by heating at temperature ranging between 383K and 423K for a period ranging between 15 to 20 hours to obtain activated carbon-metal organic framework composite materials.

In another embodiment of the present invention mole ratio of metal salt and organic ligand is in the range of 1.9 to 2.1.

In another embodiment of the present invention organic ligand used in step (a) is Benzene di- and tri-carboxylic acids.

In another embodiment of the present invention activated carbon used in step (d) is selected from the group consisting of charcoal, pet coke derived carbon, AP4-60 (Chemviron) and WS-480 (Chemviron).

In another embodiment of the present invention metal used in step (b) is Copper.

In another embodiment of the present invention yield of composite materials is in the range of 75 to 95%.

DETAILED DESCRIPTION OF THE INVENTION

Reference will now be made in detail to presently preferred embodiments and methods of the invention, which constitute the best modes of practicing the invention presently known to the inventors.

As used herein "guest" means any chemical species that resides within the void regions of an open framework solid (such as MOF) that is not considered integral to the framework. Such as molecules of the solvent (water or Dimethyl formamide) that fill the void regions during the synthetic process of MOF, other molecules that are replaced for the solvent molecules after evacuation are gases in a sorption experiment.

As used herein "void space filling agent" means a guest species that fills the void regions of an open framework during synthesis. Materials that exhibit permanent porosity remain intact even after removal of the guest species such as solvent molecules or molecular charge-balancing species via heating and/or evacuation. Sometimes, void space filling agents are referred to as templating agents.

As used herein "void space filling method" means a method by which a void space filling agent is incorporated in the porous structure usually by adding in-situ during synthesis. It can be also referred to as the method by which the under-utilized or un-used void space within the MOF is reduced by incorporation of void space filling agent thereby creating more micro porosity which contributes significantly to enhance the methane storage capacity.

MOFs are highly porous materials that can store gas molecules such as $CO_2$ and methane, readily and at high selectivity over other gases such as nitrogen. Typically the adsorption is simple physiorption. MOFs possess large pore volume which is in most of the cases remained under utilized after adsorption of gas such as methane. In the present invention it has been found that if the un-utilized void of the MOFs is reduced simply by use of void space filling method which is accomplished by incorporating certain type and amount of activated carbon as void space filling agent during the synthesis of MOFs, significantly increases the MOF's capacity for methane storage. In particular, a MOF known as Cu-BTC has been made to adsorb more methane than that synthesized without activated carbon.

Several MOFs have open metal sites (coordinatively unsaturated) that are built into the pore "walls" in a repeating, regular fashion. These metal sites, such as those found in Cu-BTC or MIL-101, have been shown to impart catalytic activity to the materials. The partial positive charges on the metal sites in MOFs also have the potential to enhance general adsorption properties. This has often been discussed as a strategy for increasing hydrogen adsorption in MOFs.

The MOFs that are useful in the present invention have large surface area, large void space/pore volume, and accessible metal sites. The major portion of void space remain under-utilized after activation i.e. removing solvent molecules or molecular charge balancing species by heating and/or evacuation, followed by gas adsorption, among such MOFs are Cu-BTC, (or HKUST-1), MOF-5, MIL-53 and MIL-101, etc. The preparation of these MOFs is described in the scientific literature.

Cu-BTC, one of the most extensively studied MOF, both experimentally and theoretically, has a face-centered cubic crystal structure and contains an intersecting 3D system of large square-shaped pores (9×9 Å) composed of paddlewheel units assembled from two copper atoms and four benzene tri-carboxylate (BTC) groups. The structure of Cu-BTC has two kinds of domains: (1) tetrahedron side pockets (~5 Å diameter with 3.5 Å windows) and large square-shaped channels. The unit cell has a free volume of 66% and a BET surface area ranging from 1200 to over 2000 $m^2/g$.

Materials Synthesis and Characterization

Figure 1:
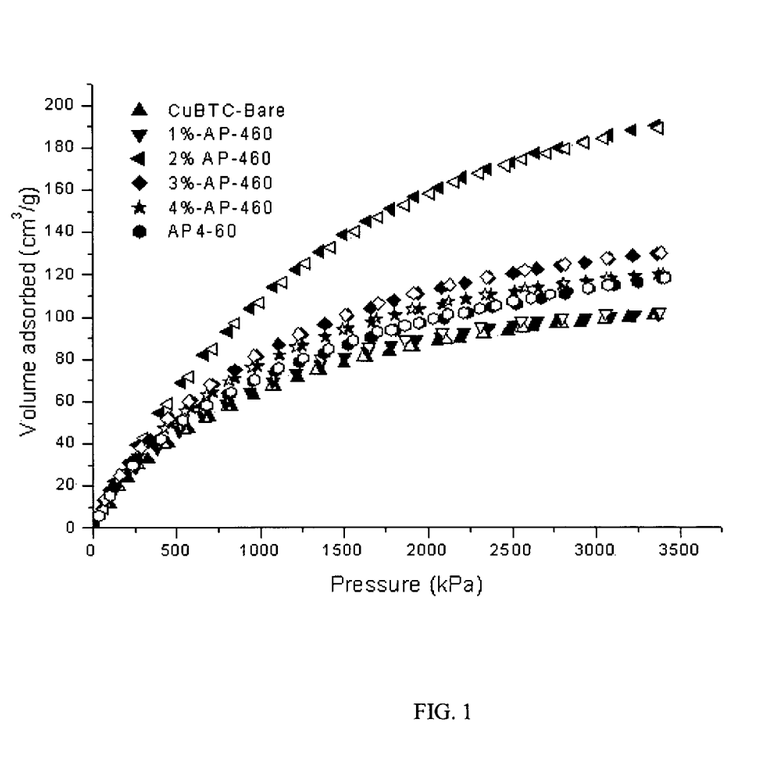
FIG. 1 shows methane adsorption-desorption isotherms at 303K on 'Cu-BTC-Bare' that has been synthesized without activated carbon, and those of composite materials synthesized using 1, 2, 3 and 4 wt % activated carbon (AP4-60, Chemviron). Closed symbols represent adsorption data and open symbols are desorption data.

Cu-BTC can be synthesized by several methods [(a) O. M. Yaghi, G. M. Li, and H. L. Li, Nature 378 (1995) 703-706; (b) S. S.-Y. Chui, S. M. F. Lo, J. P. H. Charmant, A. G. Orpen, I. D. Williams, Science 283 (1999) 1148-1150]. However, in the present invention Cu-BTC is synthesized as per the method reported by Qing Min Wang, et al. [Qing Min Wang, Dongmin Shen, Martin Bülow, Miu Ling Lau, Shuguang Deng, Frank R. Fitch, Norberto O. Lemcoff, Jessica Semanscin, Microporous and Mesoporous Materials 55 (2002) 217-230]. Furthermore, four different samples are prepared by adding varying amount of commercially available activated carbon (such as AP4-60, Chemviron) after grinding and passing through 60 BSS mesh during the synthesis of Cu-BTC. The first sample (1% AP-460@CuBTC) was prepared by loading 1 wt % of activated carbon (AP4-60) in-situ during the synthesis of Cu-BTC, the second one (2% AP-460@CuBTC) was prepared by loading 2 wt % of the same carbon, and the third one (3% AP-460@CuBTC) with a 3 wt % loading of AP4-60. Likewise, (4% AP-460@CuBTC) was prepared by 4 wt % AP4-60 loading. Over and above this, four different AC@CuBTC composite materials are prepared by adding 2 wt % each of AP4-60, WS-480, Pet coke derived activated carbon and Charcoal, during the synthesis of Cu-BTC. The experimental isotherms for methane adsorption were measured at 303K up to 4000 kPa (i.e. 40 bars) after activation of sample at 423K with continuous evacuation for overnight period using BELSORP-HP (Bell Inc., Japan). Over the pressure range examined, except the sample 1% AP-460@CuBTC, all other samples adsorb more methane than the 'CuBTC-Bare' sample (FIG. 1). In fact, the isotherms for 'CuBTC-bare' and 1% AP-460@CuBTC are overlapping indicating no enhancement in methane adsorption capacity. The 2% AP-460@CuBTC adsorbs maximum methane than all the other samples (see Table 1). It is noted that 3% AP-460@CuBTC has better adsorption capacity than 4% AP-460@CuBTC. However, both these samples have lower adsorption capacity for methane than that of 2% AP-460@CuBTC. It is inferred from FIG. 1 that loading of 2% AP-460 during synthesis resulted in 2% AP-460@CuBTC composite material which has highest methane capacity of 190.3 cc/g. Therefore, it can be used to enhance the affinity of the material for methane without affecting the desorption which is completely reversible.

Figure 3:
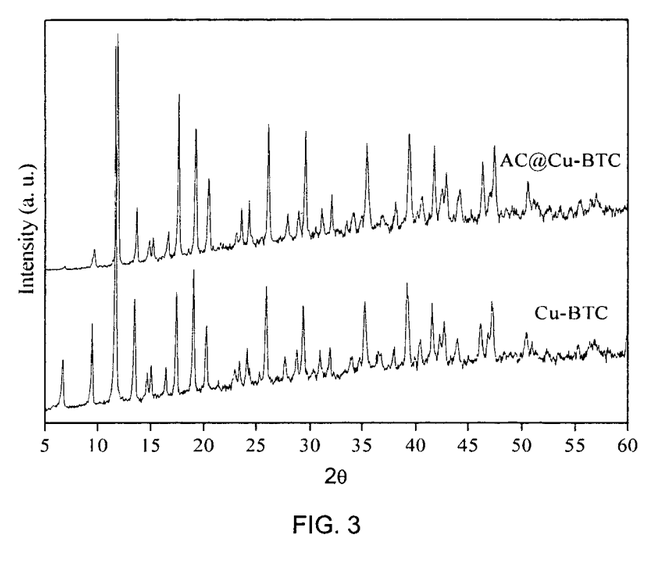
FIG. 3 Shows Powder XRD patterns of as synthesized Cu-BTC and 2% AP-460@Cu-BTC

Powder X-ray diffraction (PXRD) patterns of MOF and AC@MOF materials were recorded with a Philips X'Pert diffractometer using nickel-filtered, Cu $K_\alpha$ radiation (λ=1.5418 Å) over a range of 5 degree<2θ<60 degrees. The PXRD patterns of the as-synthesized material "CuBTC-Bare' and that of 2% AP-460@CuBTC are almost similar indicating that upon loading of the activated carbon in Cu-BTC the structure is not collapsed. However, some of the peaks are differed in intensities indicating slight distortion of the structure due to incorporation of amorphous activated carbon (FIG. 3).

Figure 2:
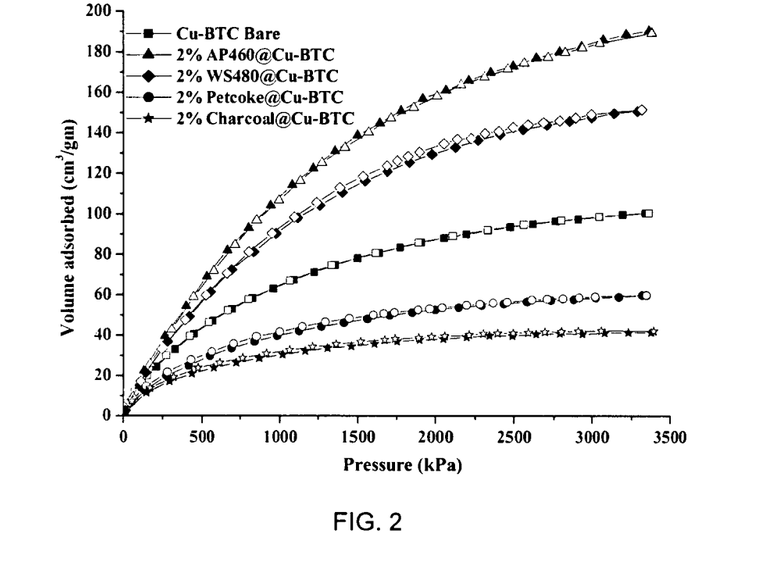
FIG. 2 Shows methane adsorption-desorption isotherms at 303K on 2% AC@Cu-BTC that has been synthesized in presence 2 wt % of different types of activated carbons (AC). Closed symbols represent adsorption data and open symbols are desorption data.
Figure 4:
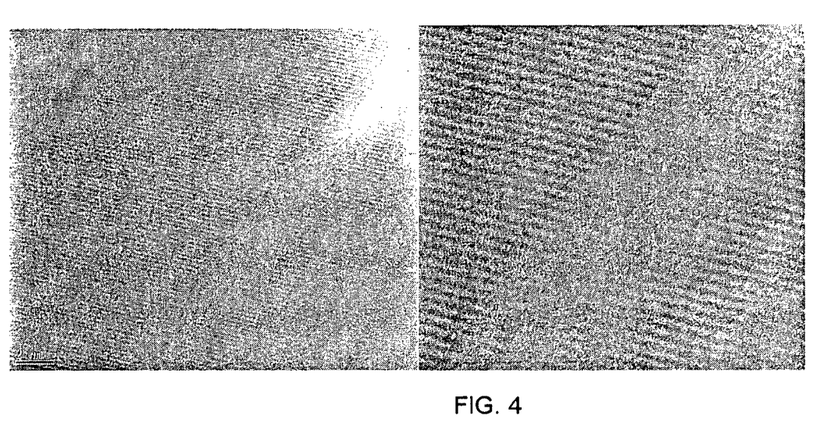
FIG. 4 Shows Transmission Electron Microscopy images of 2% AP-460@Cu-BTC.

The Transmission electron microscopy image of 2% AP-460@Cu-BTC is shown in FIG. 4. It clearly shows the lattice structure of Cu-BTC and the presence of activated carbon. The experimental isotherms for methane adsorption measured at 303K up to 4000 kPa (i.e. 40 bars) after activation of samples at 423K with continuous evacuation for overnight period using BELSORP-HP (Bell Inc., Japan) revealed that addition of 2 wt % AP4-60 only show enhancement of methane sorption capacity (FIG. 2). In contrast, use of other carbons reduce the methane capacity in the order of 2% WS-480@CuBTC>CuBTC-Bare>2% Pet coke derive carbon@CuBTC>2% Charcoal@CuBTC. It is clear from FIG. 2 that loading of 2 wt % of AP4-60 and WS-480 (Chemviron) are only enhancing the methane capacity of Cu-BTC but other carbons do not show this behavior.

The extrudes prepared using 2% AP-460@Cu-BTC prepared on 400 g/batch scale and 5 wt % CMC sodium salt as binder showed methane adsorption capacity of 142 $cm^3/g$ (Table 2). The packing density of this material is about 1.0 g/cc. Thus, the methane adsorption capacity of extrudes is 142 $cm^3/cm^3$. Such composite material may be useful in vehicular applications. To further illustrate the inventive AC@MOF composite materials and methods for making them, the following examples are given. It is to be understood that these examples are provided for illustrative purposes and are not to be construed as limiting the scope of the present invention.

EXAMPLES

Example 1

Preparation of "CuBTC-Bare"

Cu-BTC is synthesized by an improved process reported by Qing Min Wang, et al. [Qing Min Wang, Dongmin Shen, Martin Bülow, Miu Ling Lau, Shuguang Deng, Frank R. Fitch, Norberto O. Lemcoff, Jessica Semanscin, Microporous and Mesoporous Materials 55 (2002) 217-230]. The recipe is as follows.

Benzene-1,3,5-tricarboxylic acid (49.1 g, 0.234 mol) was dissolved into ethanol (250 ml), and cupric nitrate hydrate ($Cu(NO_3)_2.3.0H_2O$; 108.6 g, 0.466 mol) was dissolved into water (250 ml). The two solutions were mixed at ambient temperature (300K) for 30 min, and the mixture was transferred into an autoclave. The autoclave was heated at temperature, 393K, under hydrothermal conditions for 18 h. The reaction vessel was cooled to ambient temperature (300K), and blue crystals of Cu-BTC were isolated by filtration, and washed with water. The product was dried at 383 K, overnight. The yield was quantitative (90 g). The compound has been formulated as $[Cu_3(BTC)_2-(H_2O)_x]_n$, by elemental analysis and X-ray diffraction studies [Qing Min Wang, Dongmin Shen, Martin Bülow, Miu Ling Lau, Shuguang Deng, Frank R. Fitch, Norberto O. Lemcoff, Jessica Semanscin, Microporous and Mesoporous Materials 55 (2002) 217-230]. The as-synthesized Cu-BTC was designated as 'CuBTC-Bare'. The methane adsorption capacity of this sample is 100.4 $cm^3/g$ (Table 1).

Example 2

Preparation of 1% AP-460@CuBTC

Benzene-1,3,5-tricarboxylic acid (24.55 g, 0.117 mol) was dissolved into ethanol (125 ml), and cupric nitrate hydrate ($Cu(NO_3)_2.3.0H_2O$; 54.3 g, 0.233 mol) was dissolved into water (125 ml). The two solutions were mixed at ambient temperature (300K) for 30 min, and the mixture was transferred into an autoclave. Commercially available activated carbon AP4-60 (Chemviron) (0.375 g) was added in to the reaction mixture and mixed properly. The autoclave was heated at temperature, 393 K under hydrothermal conditions for 18 h. The reaction vessel was cooled to ambient temperature (300K), and blackish blue crystals were isolated by filtration, and washed with water. The product was dried at 383 K, overnight. The yield was quantitative (48 g). The product was designated as "1% AP-460@CuBTC". The methane adsorption capacity of this sample is 100.8 $cm^3/g$ (Table 1).

Example 3

Preparation of 2% AP-460@CuBTC

Benzene-1,3,5-tricarboxylic acid (24.55 g, 0.117 mol) was dissolved into ethanol (125 ml), and cupric nitrate hydrate ($Cu(NO_3)_2.3.0H_2O$; 54.3 g, 0.233 mol) was dissolved into water (125 ml). The two solutions were mixed at ambient temperature (300K) for 30 min, and the mixture was transferred into an autoclave. Commercially available activated carbon AP4-60 (Chemviron) (0.75 g) was added in to the reaction mixture and mixed properly. The autoclave was heated at temperature, 393 K under hydrothermal conditions for 18 h. The reaction vessel was cooled to ambient temperature (300K), and blackish blue crystals were isolated by filtration, and washed with water. The product was dried at 383 K, overnight. The yield was quantitative (50 g). The product was designated as "2% AP-460@CuBTC". The methane adsorption capacity of this sample is 190.3 $cm^3/g$ (Table 1).

Example-4

Preparation of 3% AP-460@CuBTC

Benzene-1,3,5-tricarboxylic acid (24.55 g, 0.117 mol) was dissolved into ethanol (125 ml), and cupric nitrate hydrate ($Cu(NO_3)_2.3.0H_2O$; 54.3 g, 0.233 mol) was dissolved into water (125 ml). The two solutions were mixed at ambient temperature (300K) for 30 min, and the mixture was transferred into an autoclave. Commercially available activated carbon AP4-60 (Chemviron) (1.125 g) was added in to the reaction mixture and mixed properly. The autoclave was heated at temperature, 393 K under hydrothermal conditions for 18 h. The reaction vessel was cooled to ambient temperature (300K), and blackish blue crystals were isolated by filtration, and washed with water. The product was dried at 383 K, overnight. The yield was quantitative (45 g). The product was designated as "3% AP-460@CuBTC". The methane adsorption capacity of this sample is 129.8 $cm^3/g$ (Table 1).

Example-5

Preparation of 4% AP-460@CuBTC

Benzene-1,3,5-tricarboxylic acid (24.55 g, 0.117 mol) was dissolved into ethanol (125 ml), and cupric nitrate hydrate ($Cu(NO_3)_2 \cdot 3.0H_2O$; 54.3 g, 0.233 mol) was dissolved into water (125 ml). The two solutions were mixed at ambient temperature (300K) for 30 min, and the mixture was transferred into an autoclave. Commercially available activated carbon AP4-60 (Chemviron) (1.5 g) was added in to the reaction mixture and mixed properly. The autoclave was heated at temperature, 393 K under hydrothermal conditions for 18 h. The reaction vessel was cooled to ambient temperature (300K), and blackish blue crystals were isolated by filtration, and washed with water. The product was dried at 383 K, overnight. The yield was quantitative (45 g). The product was designated as "4% AP-460@CuBTC. The methane adsorption capacity of this sample is 120.0 $cm^3/g$ (Table 1).

Example-6

Preparation of 2% WS-480@CuBTC

Benzene-1,3,5-tricarboxylic acid (24.55 g, 0.117 mol) was dissolved into ethanol (125 ml), and cupric nitrate hydrate ($Cu(NO_3)_2 \cdot 3.0H_2O$; 54.3 g, 0.233 mol) was dissolved into water (125 ml). The two solutions were mixed at ambient temperature (300K) for 30 min, and the mixture was transferred into an autoclave. Commercially available activated carbon WS-480 (Chemviron) (0.75 g) was added in to the reaction mixture and mixed properly. The autoclave was heated at temperature, 393 K, under hydrothermal conditions for 18 h. The reaction vessel was cooled to ambient temperature (300K), and blackish blue crystals were isolated by filtration, and washed with water. The product was dried at 383 K, overnight. The yield was quantitative (45 g). The product was designated as "2% WS-480@CuBTC". The methane adsorption capacity of this sample is 150.7 $cm^3/g$ (Table 2).

Example-7

Preparation of 2% Petcoke Derived AC@CuBTC

Benzene-1,3,5-tricarboxylic acid (24.55 g, 0.117 mol) was dissolved into ethanol (125 ml), and cupric nitrate hydrate ($Cu(NO_3)_2 \cdot 3.0H_2O$; 54.3 g, 0.233 mol) was dissolved into water (125 ml). The two solutions were mixed at ambient temperature (300K) for 30 min, and the mixture was transferred into an autoclave. Pet coke derived AC (prepared in our laboratory by chemical activation of pet coke with KOH) (0.75 g) was added in to the reaction mixture and mixed properly. The autoclave was heated at temperature, 393 K under hydrothermal conditions for 18 h. The reaction vessel was cooled to ambient temperature (300K), and blackish blue crystals were isolated by filtration, and washed with water. The product was dried at 383 K, overnight. The yield was quantitative (42 g). The product was designated as "2% Pet coke derived AC@CuBTC". The methane adsorption capacity of this sample is 59.8 $cm^3/g$ (Table 2).

Example-8

Preparation of 2% Charcoal@CuBTC

Benzene-1,3,5-tricarboxylic acid (24.55 g, 0.117 mol) was dissolved into ethanol (125 ml), and cupric nitrate hydrate ($Cu(NO_3)_2 \cdot 3.0H_2O$; 54.3 g, 0.233 mol) was dissolved into water (125 ml). The two solutions were mixed at ambient temperature (300K) for 30 min, and the mixture was transferred into an autoclave. Commercially available Charcoal (0.75 g) was added in to the reaction mixture and mixed properly. The autoclave was heated at temperature, 393 K, under hydrothermal conditions for 18 h. The reaction vessel was cooled to ambient temperature (300K), and blackish blue crystals of Cu-BTC were isolated by filtration, and washed with water. The product was dried at 383 K, overnight. The yield was quantitative (40 g). The product was designated as "2% Charcoal@CuBTC. The methane adsorption capacity of this sample is 41.3 $cm^3/g$ (Table 2).

Example-9

Preparation of 2% AP-460@CuBTC (Scale up)

Benzene-1,3,5-tricarboxylic acid (245.5 g, 1.17 mol) was dissolved into ethanol (1250 ml), and cupric nitrate hydrate ($Cu(NO_3)_2 \cdot 3.0H_2O$; 543 g, 2.33 mol) was dissolved into water (1250 ml). The two solutions were mixed at ambient temperature (300K) for 30 min, and the mixture was transferred into an autoclave. Commercially available activated carbon AP4-60 (Chemviron) (7.5 g) was added in to the reaction mixture and mixed. The autoclave was heated at temperature, 393 K, under hydrothermal conditions for 18 h. The reaction vessel was cooled to ambient temperature (300K), and blackish blue crystals were isolated by filtration, and washed with water. The product was dried at 383 K, overnight. The yield was quantitative (450 g). The product was designated as "2% AP-460@CuBTC (Scale up). The methane adsorption capacity of this sample is 156.9 $cm^3/g$ (Table 2).

Example-10

Preparation of Extrudes of 2% AP-460@CuBTC (Scale up)

The product "2% AP-460@CuBTC (Scale up)" (400 g) is mixed with 20 g of carboxy methyl cellulose sodium salt (CMC-sodium salt) and sufficient quantity of deionized water is added to form dough like extrudable mass. It was kneaded properly to form uniform dough like mass. The mass is then extruded using a kitchen machine. Alternately, a single screw type Micro extruder fitted with axial discharge system can also be used for the purpose. The extrudate (2-3 mm diameter) thus prepared is dried first at room temperature and then at 383K for overnight period. It was broken in small pieces manually to obtain extrudes with the length in the range 4-6 mm. The methane adsorption capacity of extrudes is 142.0 $cm^3/g$ (Table 3). The packing density of this extrudes is determined to be ~1.0 g/cc. Thus, the extrudate is having 142.0 $cm^3/g$ methane adsorption capacity (Table 2).

TABLE 1

Methane adsorption capacity of CuBTC-Bare and those of AP-460@CuBTC with different amount of AP4-60

| Sample | Methane adsorption capacity at 3500 kPa, 303 K |
|---|---|
| CuBTC-Bare | 100.4 |
| 1% AP460@Cu-BTC | 100.8 |
| 2% AP460@Cu-BTC | 190.3 |
| 3% AP460@Cu-BTC | 129.8 |

TABLE 1-continued

Methane adsorption capacity of CuBTC-Bare and those of
AP-460@CuBTC with different amount of AP4-60

| Sample | Methane adsorption capacity at 3500 kPa, 303 K |
|---|---|
| 4% AP460@Cu-BTC | 120.0 |
| AP4-60 | 118.0 |

TABLE 2

Methane adsorption capacity of AC@CuBTC with
different types of activated carbons

| Sample | Methane adsorption capacity at 3500 kPa, 303 K |
|---|---|
| CuBTC-Bare | 100.4 |
| 2% AP-460@Cu-BTC | 190.3 |
| 2% WS-480@Cu-BTC | 150.7 |
| 2% Pet coke carbon@Cu-BTC | 59.8 |
| 2% Charcoal@Cu-BTC | 41.3 |
| 2% AP-460@Cu-BTC (Scale up) | 156.9 |
| Extrudes of 2% AP-460@Cu-BTC (scale up), Prepared using 5% CMC-sodium salt | 142.0 |

Advantages of Present Invention

In the present invention, we disclosed the successful enhancement of gas adsorption capacity, by synthesizing activated carbon-metal organic framework composite material, such as AC@CuBTC. The process of preparing the composite material is simple and easy to perform as it involve only one more step i.e. addition of selected type and appropriate amount of activated carbon, readily available in the market, in-situ during the conventional synthesis of metal organic frame work material. This process eliminates the post synthesis treatment required for the enhancement of gas adsorption capacity as reported by other researchers. The under-utilized pore or void space volume have been filled with activated carbon so that the affinity for methane is increased without changing the original structure of MOF. The quantity of activated carbon required to enhance the methane adsorption capacity is very small and therefore do not contribute much in cost of production. This will be very advantageous for commercial production of such methane storage material for vehicular applications. Furthermore, the implications and scope of such synthesis process are revealed by the methane sorption properties of several activated carbon-MOF composite materials, where, the highest methane storage capacity obtained for composite powder is 190.3 $cm^3/g$ which is very close to that of carbon (200 $cm^3/g$) reported in the literature, and the packing density of material has been determined to be about 1.0 $g/cm^3$. Thus, its V/V capacity would be the same as $cm^3/g$ which is most desirable to provide a material having advantageously enhanced methane adsorption capacity. Yet further advantage is that the process can be scaled up to produce composite material. It is also possible to form shaped body such as extrude of AC@MOF using binder such as CMC-sodium salt which is also available commercially and the amount of binder used is merely 5 wt %. Still further, it would be advantageous to provide such a composite material which can advantageously store gases at desirable pressures such as the predominant natural gas methane.

We claim:

1. A process for the preparation of an activated carbon-metal organic framework composite material with enhanced gas adsorption capacity and having activated carbon from 1 wt % to 4 wt %, wherein the said process comprising the steps:
  a. dissolving an organic ligand in ethanol;
  b. dissolving a metal salt in the water;
  c. mixing the solution as obtained in step (a) with solution as obtained in step (b) followed by stirring at temperature ranging from 298K to 308K for a period ranging between 10 to 50 min;
  d. transferring the reaction mixture as obtained in step (c) into an autoclave and further adding activated carbon in the range 1 to 4 wt % in respect of weight of product followed by heating at temperature ranging between 383K and 423K for a period ranging between 15 to 20 hours to obtain an activated carbon-metal organic framework composite material.

2. The process as claimed in claim 1, wherein the mole ratio of metal salt and organic ligand is in the range of 1.9 to 2.1.

3. The process as claimed in claim 1, wherein the organic ligand used in step (a) is 1.3.5-Benzene tri-carboxylic acids.

4. The process as claimed in claim 1, wherein the activated carbon used in step (d) is a porous pelletized activated carbon or a high activity virgin pelletized activated carbon.

5. The process as claimed in claim 1, wherein the metal used in step (b) is Copper.

6. The process as claimed in claim 1, wherein the yield of composite materials is in the range of 75 to 95%.

* * * * *